US012308124B2

(12) United States Patent
Cray et al.

(10) Patent No.: US 12,308,124 B2
(45) Date of Patent: *May 20, 2025

(54) SYSTEMS AND METHODS FOR ALLOCATING RESOURCES IN MENTAL HEALTH TREATMENT

(71) Applicant: Mental Health Technologies, Inc., Aurora, IL (US)

(72) Inventors: John Cray, Naperville, IL (US); Ernesto Wallerstein, Jr., North Aurora, IL (US)

(73) Assignee: Mental Health Technologies, Inc., Aurora, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/497,071

(22) Filed: Oct. 30, 2023

(65) Prior Publication Data

US 2024/0062914 A1 Feb. 22, 2024

Related U.S. Application Data

(63) Continuation of application No. 17/383,819, filed on Jul. 23, 2021, now Pat. No. 11,894,146.

(Continued)

(51) Int. Cl.
*G16H 50/30* (2018.01)
*G06N 3/02* (2006.01)
(Continued)

(52) U.S. Cl.
CPC .............. *G16H 50/30* (2018.01); *G06N 3/02* (2013.01); *G16H 10/20* (2018.01); *G16H 10/60* (2018.01); *G16H 40/20* (2018.01); *G16H 50/70* (2018.01)

(58) Field of Classification Search
CPC ........ G16H 50/30; G16H 10/20; G16H 10/60; G16H 40/20; G16H 50/70; G16H 20/70; G06N 3/02; G06N 3/044; G06N 3/08
See application file for complete search history.

(56) References Cited

U.S. PATENT DOCUMENTS 9,728,101 B2   8/2017 Osborn
11,568,979 B1   1/2023 Granato
(Continued)

OTHER PUBLICATIONS

Office Action issued in U.S. Appl. No. 17/383,819, mailing date Jul. 6, 2023.
(Continued)

*Primary Examiner* — Meredith A Long
(74) *Attorney, Agent, or Firm* — Benjamen E. Kern; Thomas Y. Kendrick; Kern Kendrick, LLC (57) ABSTRACT

A computer implemented method for allocating resources in mental health treatment includes the steps of: retrieving individual patient's mental health assessment data mapped to assessed mental conditions; computing a wellness score of the mapped assessed mental conditions; determining an overall treatment efficacy progress with a statistically analyzed gradient of the wellness scores; aggregating over a pool of patients population with similar conditions, a distribution of the gradient of the computed wellness scores of an overall treatment efficacy progress; sampling over a defined range of the distribution of the gradient of the computed wellness scores to determine a correlation coefficient of fixed factors and variable factors; using correlated coefficient of fixed factors and variable factors to assess efficacy of mental health treatment regimens for adjusting available mental health treatment resources to determine a next mental health treatment regimen; and communicating the next mental health treatment regimen to a healthcare provider.

20 Claims, 7 Drawing Sheets

Related U.S. Application Data (60) Provisional application No. 63/055,685, filed on Jul. 23, 2020.

(51) Int. Cl.
*G16H 10/20* (2018.01)
*G16H 10/60* (2018.01)
*G16H 40/20* (2018.01)
*G16H 50/70* (2018.01)

(56) References Cited

U.S. PATENT DOCUMENTS

| | | | |
|---|---|---|---|
| 11,894,146 B2 * | 2/2024 | Cray | G16H 40/20 |
| 2006/0241972 A1 | 10/2006 | Lang | |
| 2010/0249531 A1 | 9/2010 | Hanlon et al. | |
| 2015/0356250 A1 | 12/2015 | Polimeni | |
| 2019/0026438 A1 | 1/2019 | Ma et al. | |
| 2019/0043623 A1 | 2/2019 | Wallington, IV | |
| 2019/0083021 A1 | 3/2019 | Hamilton | |
| 2019/0392466 A1 | 12/2019 | Chamberlain et al. | |
| 2020/0090812 A1 | 3/2020 | Condie et al. | |
| 2020/0118458 A1 | 4/2020 | Shriberg et al. | |
| 2020/0152320 A1 | 5/2020 | Ghazaleh | |
| 2021/0241137 A1 | 8/2021 | Jain et al. | |
| 2021/0342545 A1 | 11/2021 | Avshalomov | |
| 2022/0223399 A1 | 7/2022 | Kaushal et al. | |
| 2022/0319705 A1 | 10/2022 | Feuerstein | |
| 2023/0042882 A1 | 2/2023 | Griffin | |

OTHER PUBLICATIONS

International Search Report and Written Opinion issued on Feb. 18, 2015 in PCT/US2024/059081.

* cited by examiner

John GAD-7 ASSESSMENT RESULTS
GAD-7 Assessment Results

| | | | |
|---|---|---|---|
| Patient Name | Bill | Date/Time | 05/202/2020 |
| Gender | Male | Completion Time | 0H 0M 12s |
| Facility | MHT Test Clinic 1 | Height/Weight | --ft / --kg |
| Patient MRN | 1001001 | Blood Pressure | -- |
| Clinician | Clinic Clinician | | |

Generalized Anxiety Assessment

| Question | Not At All | Several Days | More Than Half the Days | Nearly Every Day |
|---|---|---|---|---|
| 1. Feeling nervous, anxious or on edge | | ⊙ | | |
| 2. Not being able to stop or control worrying | | ⊙ | | |
| 3. Worrying too much about different things | | ⊙ | | |
| 4. Trouble Relaxing | | | ⊙ | |
| 5. Being so restless that it is hard to sit still | | | ⊙ | |
| 6. Becoming easily annoyed or irritable | | | ⊙ | |
| 7. Feeling afraid as if something awful might happen | | | ⊙ | |

| Question | Not Difficult At All | Somewhat Difficult | Very Difficult | Extremely Difficult |
|---|---|---|---|---|
| 8. How difficult have these problems made it for you to do your work, take care of things at home, or get along with other people? | | | ⊙ | |

Over all

Level of Anxiety: Moderate   Score: 11/21

[ Minimal 0-4 ]  [ Mild 5-9 ]  [Moderate 10-14]  [Severe 15-21]

Functional Impairment: Very Difficult

Notes
---

Assessment History        Score
05/19/20, 10:56 PM        11
05/19/20, 09:44 PM        11

SYSTEMS AND METHODS FOR ALLOCATING RESOURCES IN MENTAL HEALTH TREATMENT

CROSS-REFERENCE

The present application is a continuation of U.S. patent application Ser. No. 17/383,819, filed on Jul. 23, 2021, which claims priority from U.S. Provisional Patent Application No. 63/055,685, filed on Jul. 23, 2020, each of which is hereby incorporated by reference in its entirety for all purposes.

TECHNICAL FIELD

The present application relates to system and methods for allocating resources in mental health treatment in population.

BACKGROUND

In the field of mental health, standardized, question-based testing may be used to assess patient status for specific mental health conditions, such as anxiety, depression, obsessive compulsive disorder, bipolar disorder, substance abuse, suicide risk severity, and many others. These mental health assessments may be administered to patients as part of a clinical treatment program to determine condition severity levels during admission, and/or on a regular basis to show progress over time. Testing may be applied to any age group which may be found to be particularly useful in assessing adolescent and pre-adolescent individuals for ADHD, depression and other conditions; these are sometimes taken or brokered by an intermediary, such as a parent, guardian or teacher. Additionally, since these tests may be standardized and recognized by various health organizations, and may be covered as a reimbursable component of treatment by most insurers, assessments may be used by any group wishing to measure a status of the individuals within a community, including clinics, schools, corporate wellness programs, government divisions, and so on. Nevertheless, the traditional mental health treatment methods are time consuming and slow to manifest the results to legitimize efficacy, limiting insights to model or to focus study on factors to optimize resources to treatment regimen for efficacy progress.

SUMMARY

A method for allocating resources to mental health treatment, including: collecting individual patient mental health assessment data from among a plurality of individuals, including adults, adolescents and/or pre-adolescents. The method for determining allocation of resources in mental health treatment may be a computer implemented method, which is executed by at least one processor on a computing layer, an algorithm stored on a non-transitory computer-readable memory medium that communicates mental health treatment resources allocation after analyzing to a healthcare provider. The mental health treatment resources allocation include the steps of: (a) retrieving, from a database layer that stores individual patients' profiles and corresponding electronic medical record, a patient's mental health assessment data stored according to a profile of the patient, wherein the patient's mental health assessment data includes a plurality of symptoms categories data that have been mapped to one or more assessed mental conditions; (b) computing, a wellness score for the patient, by aggregating each and every individual weighted score of the mapped assessed mental condition of the patient; (c) determining, an overall treatment efficacy progress for the patient, by statistically analyzing a gradient of the computed wellness scores of the individual patient over a time duration; (d) aggregating, over a pool of patients population with similarly mapped assessed mental conditions, a distribution of the gradient of the computed wellness scores of an overall treatment efficacy progress; (e) sampling over a defined range of the distribution of the gradient of the computed wellness scores of the overall treatment efficacy progress to determine a correlation coefficient of fixed factors and variable factors that affect the overall treatment efficacy progress within the pool of patients population, wherein the fixed factors are factors that do not change from assessment to assessment while variable factors are factors that can change from assessment to assessment; (f) using both the correlated coefficient of fixed factors and variable factors to compare or adjust treatment efficacy over a range of available mental health treatment resources including resources that have not been previously allocated in order to determine a next mental health treatment regimen with an optimal overall efficacy progress over a next time duration for the patient; and (g) communicating the next mental health treatment regimen, along with a level of confidence factor, to a healthcare provider for requesting the resources for the patient.

BRIEF DESCRIPTION OF EMBODIMENTS

The disclosure may be better understood with reference to the following drawings and description. The elements in the figures are not necessarily to scale, emphasis instead being placed upon illustrating the principles of the disclosure. Moreover, in the figures, like-referenced numerals may designate to corresponding parts throughout the different views.

Most organizations providing treatment for mental health conditions have not historically used standardized mental health assessments as a systematic approach to measure progress of patients on specific treatment regimens. However, with the emergence of automation and Internet-based communications to enable an easier collection of this information from patients or delegated intermediaries, coupled with available integration methods to connect this information with data from other systems such as Electronic Medical Record (EMR) and Electronic Health Record (EHR) systems, the efficacy of these measurements has increased over time. As collection and integration methods have become more available, the ability to collect large datasets for deep learning that allow analysis of the effectiveness of treatment approaches across time periods for resource allocation is possible.

A key factor in leveraging standardized test results may determine whether patients are improving over time when subject to a well-defined treatment regimen, such as a particular type of therapy or prescribed pharmaceutical dosage range. In order to assess the effectiveness of treatment across a large patient population, a linear regression model may be applied to each patient to determine their individual rate of change for a fixed period of time (after start of treatment). This rate may then be averaged across the larger, defined population to summarize overall treatment effectiveness.

Additionally, there is a growing prevalence of available data that objectively measure a patient's physiological state, either at defined discrete intervals via physical encounters or on a more continuous basis via regular monitoring. Vital signs such as blood pressure and heart rate may be obtained from EMR and EHR systems; heart rate variability (HRV) and breathing rate variability over time may be obtained from smartwatch technologies; other indicators of stress may be obtained from voice analysis or facial analysis (e.g., from eye blink rates or jaw clenching). If this data is available via opt-in from patients and clinics, it may provide reinforcement for change results in the collected data from mental health questionnaires. For example, clinical research may indicate a correlation between lowered stress levels and lowered blood pressure and/or a higher HRV rate. Although the physiological measurements do not currently provide an objective absolute predictor of mental health states, when the physiological measurements changes are combined with rates of change in question-based assessments, they may provide a higher degree of confidence in patient treatment results.

The above test and measurement datasets may be combined with demographic data on patients, such as gender, ethnicity, geographic location, height, weight and age; other health-related data, such as disease, obesity, high blood pressure and addiction; and situational data, such as marital status, education level, income and employment status. The datasets must be anonymized to remove specific patient identification information, allowing the analysis of data in aggregated form, without violating the Health Information Portability and Accountability Act (HIPAA).

It is therefore possible to provide a system that collects the cumulative results of mental health state changes for a specific patient treatment regimen across hundreds or thousands of patients in a given defined population. This system may enable question-based assessment data to be reinforced with physiological data, indicating overall positive or negative correlation. Once this data is collected and collated, it may then be analyzed and visualized to determine correlation for any selected population variable with other fixed factors, for example, gender, occupation, age ranges overall, or age ranges for a specific ethnicity.

The capability to determine the effectiveness of mental health treatment approaches, such as a specific type of therapy or the administration of a particular drug in a particular dosage range, would be of value to clinics and mental health treatment organizations such as addiction centers or other counseling groups. For example, a mental health clinic may compare their clinical approach for teen-aged patients of Hispanic descent to benchmark data aggregated across many other mental health groups across the country. Likewise, the comparison may be performed on other ethnic groups, and based on their demographic data, such as immigrants from a certain country or a certain region of the world, and based on their income level, education background, social economic background and religious beliefs, etc.

An analysis that shows presence, change and cost of mental health conditions for a specific community, in comparison to other communities, may have value for county, state or federal government organizations to target economic improvement programs, for education and childcare to help the communities to succeed and thrive in a long term goal that may reduce poverty and reduce certain chronic diseases in the population. The analysis may be useful for insurers' evaluating coverage of clinical approaches; for corporations seeking to improve employee wellness and a healthier workforce; for schools assessing at-risk student populations; for child welfare groups monitoring emerging conditions in pre-adolescents; for early intervention to childhood learning, for facilities promoting wellness in elderly populations; for research groups studying treatment effectiveness across communities; and for various other types of organizations.

Figure 1A:
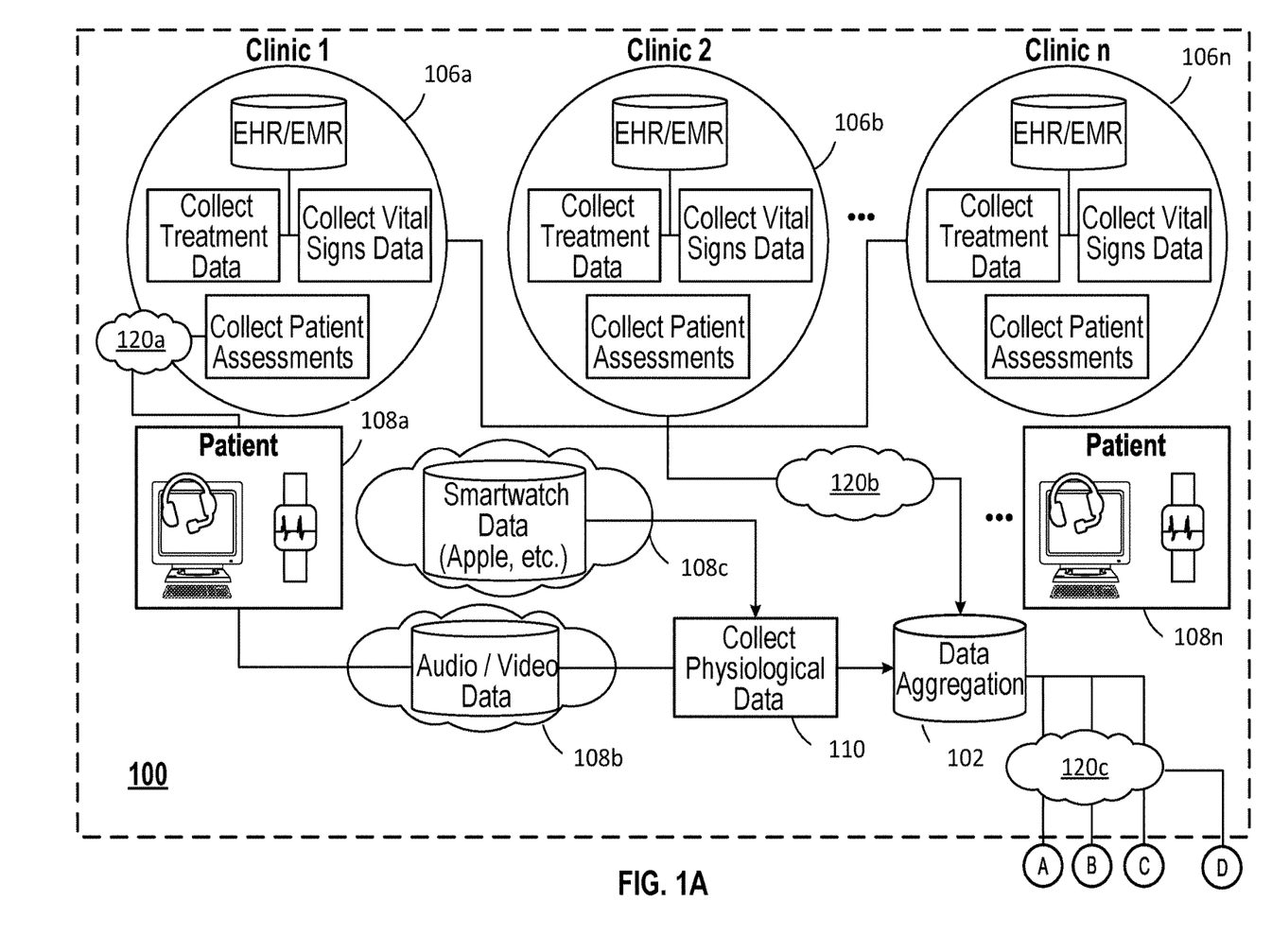
FIGS. 1A and 1B depict an example of a system to carry out mental health treatment resource allocation.
Figure 1B:
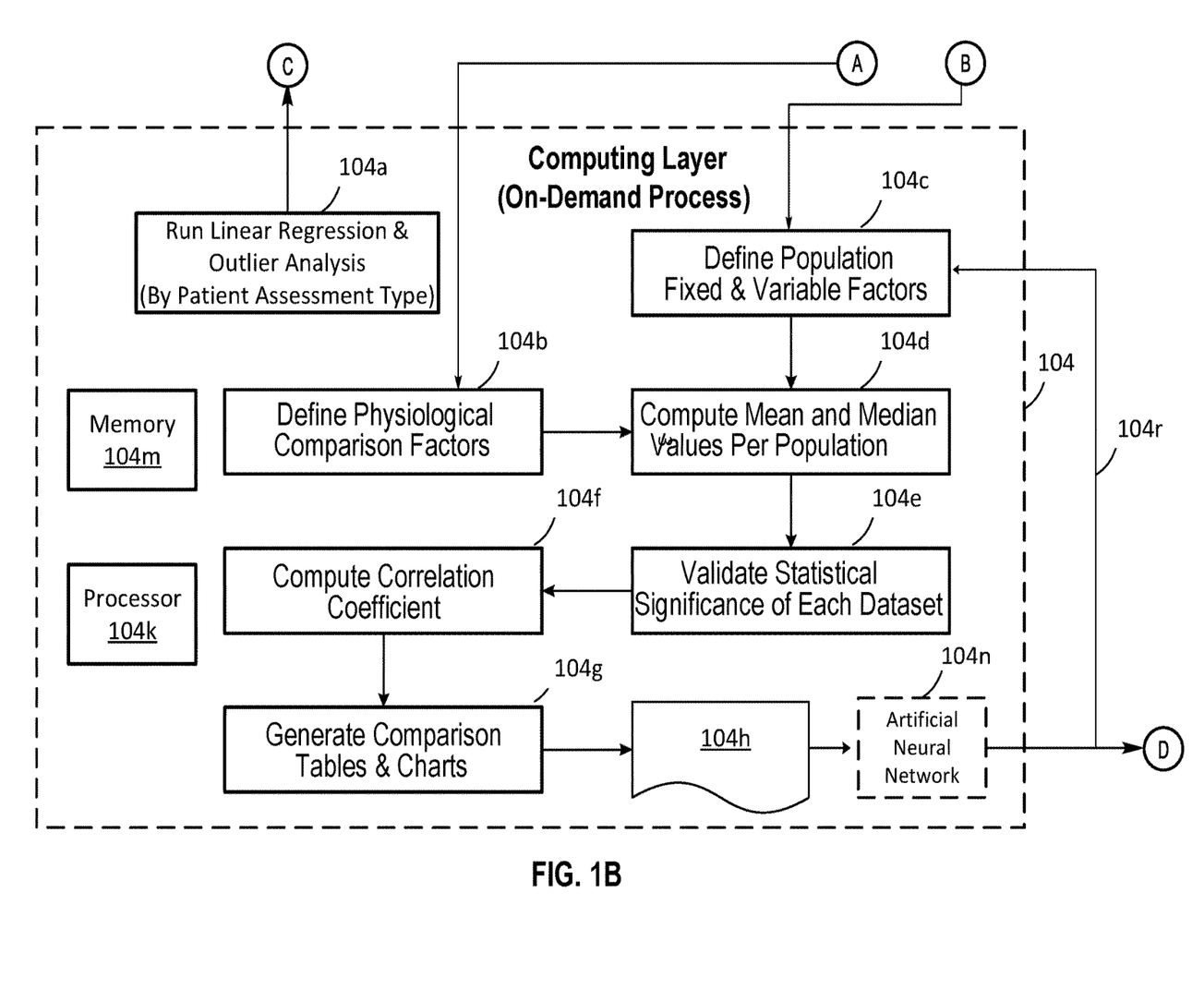

FIGS. 1A and 1B depict an example of a system 100 to carry out mental health treatment resource allocation. In an example, the system 100 may include: network 120a to 120c that enables communication among a computing layer 104, a database layer 102 that stores collected patient mental health assessment data 110 from a plurality of devices from one or a combination of: the patient (108a to 108n), the health care provider and/or authorized responder intermediaries (106a to 106n).

In implementation, the plurality of devices (104, 106a-106n, 108a-108n, 110) of the system 100 in FIG. 1A may perform the following functions including continuously collecting, aggregating and analyzing ongoing assessment data collection. The functions performed by the plurality of devices (104, 106a-106n, 108a-108n, 110) may include at least: collecting patient assessments—the system 100 may support methods (see FIG. 1C) to enable clinics (of any type) to systematically assign standardized mental health assessments (see FIG. 2) to patients or to patient intermediaries (for children, elders or others unable to handle the process without assistance), on a regular basis over an extended period of time. The mental health assessments may be available in the public domain, which assess various mental health conditions, including anxiety, depression, OCD, ADHD, addiction, bipolar disorder, suicidal risk, and many others. The system 100 may optimize collection of results by the following exemplary steps: (a) Enabling clinics to run assessments on demand or on a scheduled basis, with timing or frequency recommended or calculated based on past history and weighted specific conditions, based on a fixed schedule or based on an algorithmic determination of an optimal schedule from patient prior assessment results and trends. The assessment data collection may include collecting Medical, Situational and Demographic Information on Patients. The system 100 may enable collection of a number of data elements specific to each patient and/or assessment (with patient-provided permissions) via use of published APIs from other applications and databases, including clinic Electronic Health Record (EHR) or Electronic Medical Record (EMR) systems, clinic-operated communications and measurement systems, social media applications, and wearable device interfaces (e.g., smart watch data 108c). These APIs are typically web services based and accessible via standard Internet-based connectivity. Data on specific treatment regimens may be collected, along with start, change, and/or end dates of treatment. Additional data associated with a specific assessment which may include presence of comorbid disease or condition; wearable-collected data such as heart rate variability or breathing rate; and/or clinic-gathered data such as weight, blood pressure, voice analysis or facial analysis. Patient demographic data may include gender, ethnicity, marital status, height, employment status, income, geographic location, and others. (b) Distributing assessments to patients or intermediaries on any device, for completion in office, at home or in any Internet-available location. (c) Gathering assessment results in a structured, relational database, including calculated levels of mental health disorder. All collected data may be aggregated in a secure, relational database. Patient data is anonymized to remove name and clinic-specific Medical Record Numbers (MRNs); these are replaced by a system-generated patient-specific identifier, which may be needed to ensure subsequent patient assessment scores are continuously associated with the same patient. The aggregation of assessment data to define Physiological Comparison Factors (block 104b) may include the system 100 enables a user to select from various stored physiological factors (e.g., smart watch data 108c), which may be used to supplement the conclusions of the analysis in the final results. For example, if heart rate variability (HRV) and blood pressure are selected, an increase in HRV and a decrease in blood pressure over a patient population with lowering anxiety levels may be considered to be positively reinforcing the results of the analysis. (d) Viewing (acceptance) of results by mental health professionals.

FIG. 1B depicts an example of the functional blocks performed by the computing layer 104. The functional blocks of the computing layer 104 may include at least one processor 104a which executes an algorithm stored on a non-transitory computer-readable memory medium 104m that communicates mental health treatment resources allocation after analyzing to a healthcare provider (e.g., physician, psychiatrist, psychologist, counselor, etc.). The algorithm may enable a Define Physiological Comparison Factors block 104b of the computing layer 104 and the Define Population Fixed and Variable Factors block 104c to communicate with the database layer 102 to receive the assessment data of a patient for mapping and determination of a wellness score, extraction of correlated fixed and variable coefficient factors, and send the results to a Compute Mean and Median Values Per Population block 104d for statistically analyzing a gradient of the computed wellness scores of the patient over a time duration. A linear regression (block 104a) may be run to aggregate, over a pool of patients population with similarly mapped assessed mental conditions, a distribution of the gradient of the computed wellness scores of an overall treatment efficacy progress. The results may be sent to a Validate Statistical Significance of Each Dataset block 104e for sampling over a defined range of the distribution of the gradient of the computed wellness scores of the overall treatment efficacy progress. The results may be sent to a Compute Correlation Coefficient block 104f to determine a correlation coefficient of fixed factors and variable factors that affect the overall treatment efficacy progress within the pool of patients population. The results may be sent to a Generate Comparison Tables and Charts block 104g to compare segmented results, with usage to determine a next mental health treatment regimen with an optimal overall efficacy progress over a next time duration for the patient, using both the correlated coefficient of fixed factors and variable factors to adjust over a range of available mental health treatment resources including resources that have not been previously allocated. The output 104h may be communicated to a healthcare provider for advising on the resources for the patient in the next mental health treatment regimen. Optionally, the output 104h may be used for training an ANN 104n to optimize the treatment regimen and predict an optimal treatment regimen by comparing with a pool of the population, a deviation of efficacy in certain mapped symptoms according to the correlated coefficient of fixed factors and variable factors.

Figure 1C:
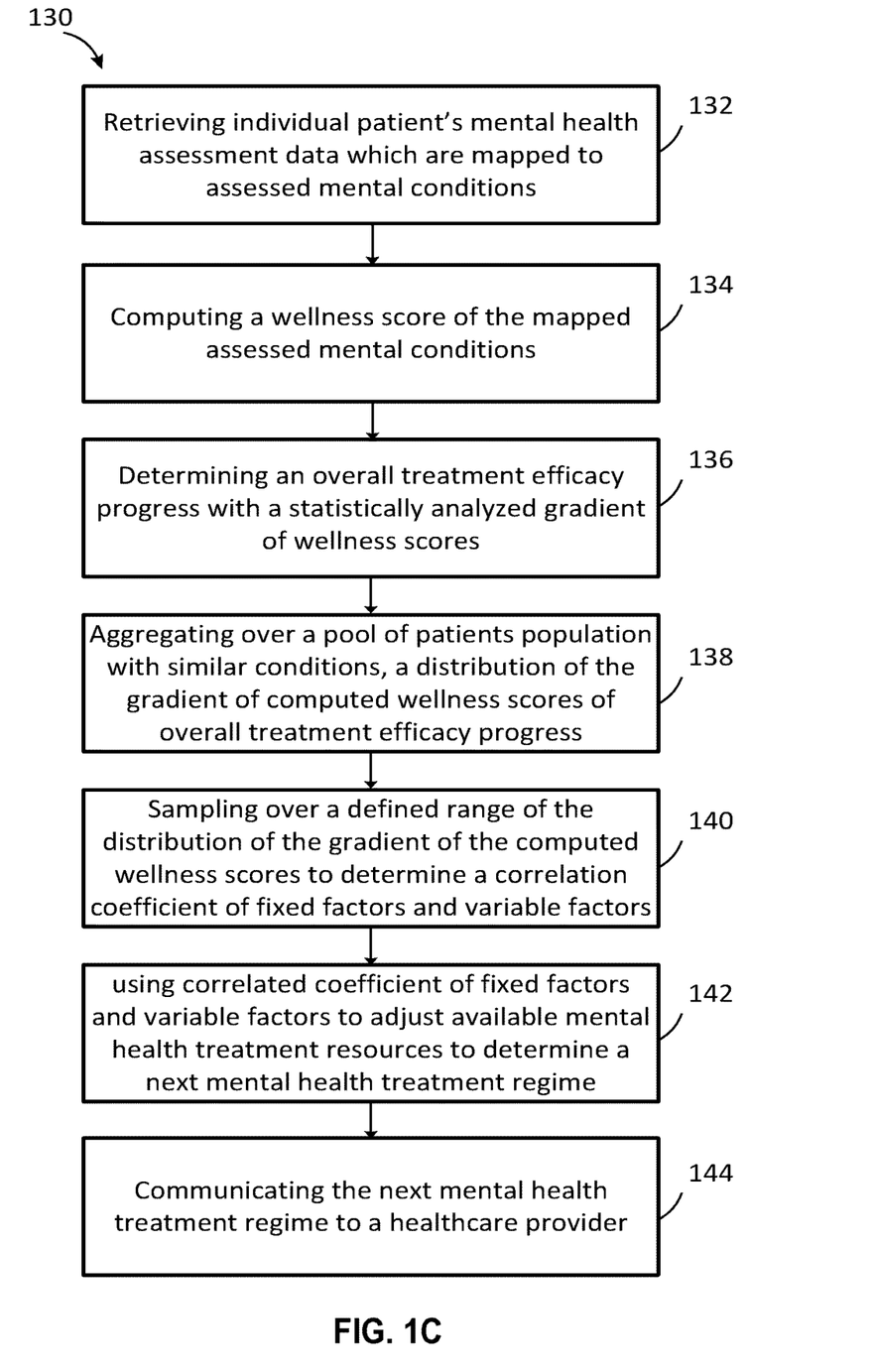
FIG. 1C depicts a computer implemented method to carry out mental health treatment resource allocation.

FIG. 1C depicts a computer implemented method 130 to carry out mental health treatment resource allocation. The computer implemented method 130 may be executed by at least one processor 104k on a computing layer 104, an algorithm stored on a non-transitory computer-readable memory medium 104m that communicates mental health treatment resources allocation to a healthcare provider, wherein the mental health treatment resources allocation algorithm may include performing the following steps:

In step 132, the computing layer 104 may perform retrieving, from a database layer 102 that stores individual patients' profiles and corresponding electronic medical record 103a-103n, a patient's mental health assessment data 105a-105n stored according to a profile of the patient, wherein the patient's mental health assessment data 105a-105n may include a plurality of symptoms categories data that have been mapped to one or more assessed mental conditions.

In step 134, the computing layer 104 may perform computing, a wellness score for the patient, by aggregating each and every individual weighted score of the mapped assessed mental condition of the patient.

In step 136, the computing layer 104 may perform determining, an overall treatment efficacy progress for the patient, by statistically analyzing a gradient of the computed wellness scores of the patient over a time duration.

In step 138, the computing layer 104 may perform aggregating, over a pool of patients population with similarly mapped assessed mental conditions, a distribution of the gradient of the computed wellness scores of an overall treatment efficacy progress.

In step 140, the computing layer 104 may perform sampling over a defined range of the distribution of the gradient of the computed wellness scores of the overall treatment efficacy progress to determine a correlation coefficient of fixed factors and variable factors that affect the overall treatment efficacy progress within the pool of patients population, wherein the fixed factors are factors that do not change from assessment to assessment while variable factors are factors that can change from assessment to assessment.

In step 142, the computing layer 104 may perform using both the correlated coefficient of fixed factors and variable factors to adjust over a range of available mental health treatment resources including resources that have not been previously allocated in order to determine a next mental health treatment regimen with an optimal overall efficacy progress over a next time duration for the patient.

In step 144, the computing layer 104 may perform communicating the next mental health treatment regimen to a healthcare provider for requesting the resources for the patient.

In implementation, the retrieved patient mental health assessment data may be priory collected from devices from one or a combination of: the patient, the health care provider and an authorized responder intermediary (parents, guardians, school counselors, etc.), and the patient's mental health assessment data may include one or more of following information: standardized questionnaire responses, gathered directly from patients or from their designated responders; physiological vital signs measurements by clinical devices or instruments; drug treatment clinical data; behavioral or mood observation data, learning disabilities or speech delays in childhood or adolescence; substance abuse or chemical dependence, physical gestures, observed physical abuse or self-inflicted wounds; and social media blogs that may contain contextual content manifesting symptoms of mental distress, aggressiveness, depression, or suicidal thoughts. The frequency and timing of assessment data collection is recommended and automated by the system, using past results along with weighted categories, such as suicidality, that guide assessment frequency.

The patient's profile may include at least one or more of the following applicable information: name, age, gender, residence geographic location, ethnicity, marital status, education level, employment status, income level, and the patient mental health assessment data comprising medication information, physical health data, obesity, mental health history, physiological data, history of substance abuse, family healthy history, anxiety, depression, attention-deficit/hyperactivity disorder (ADHD), obsessive compulsive disorder (OCD), substance addiction, bipolar disorder, suicidal thoughts, trauma, and significant life events, to name a few.

In practice, an identity of the patient may be masked from public or replaced with a unique but anonymous personal identification for privacy protection. The method may perform the following steps for optimizing resource allocation: (a) enabling clinics to run assessments on demand or on a scheduled basis; (b) distributing assessments to patients or designated intermediaries on the communication device, for completion in office, at home or in any Internet-available location; (c) gathering assessment data in a structured, relational database, including calculated levels of mental health disorder; (d) viewing of results by mental health professionals.

In practice, the collecting of the patient mental health assessment data may include collecting through an Electronic Medical Record (EMR) or Electronic Health Record (EHR) systems; the physiological vital signs measurements by clinical devices or instruments may include one or more of: blood pressure, heart rate; heart rate variability (HRV) and breathing rate variability. the physical gesture observations may include one or more of: voice analysis, eye blink rates and jaw clenching. In an example, the computing of the wellness score for the patient may include assigning a weight to each category of information in the patient mental health assessment data and computing a weighted sum.

Figure 2:
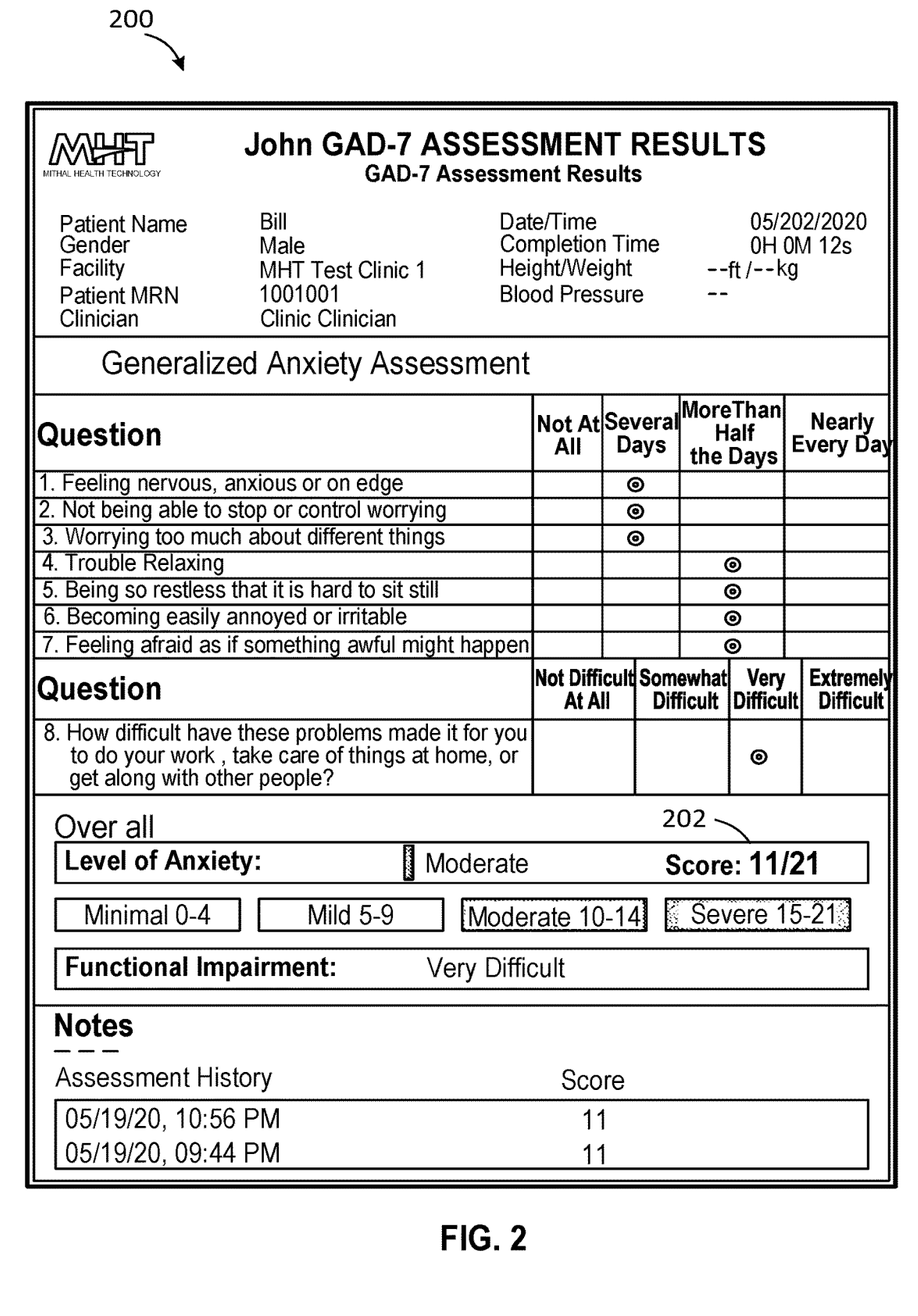
FIG. 2 depicts an example of a patient's mental health assessment data.

FIG. 2 depicts an example of a patient's mental health assessment data. FIG. 2 shows displayed results for a standardized anxiety assessment, such as the GAD-7, as collected for a patient. In this example, it is shown that the assessment has a Level of Anxiety score of 11 (out of 21).

Figure 3:
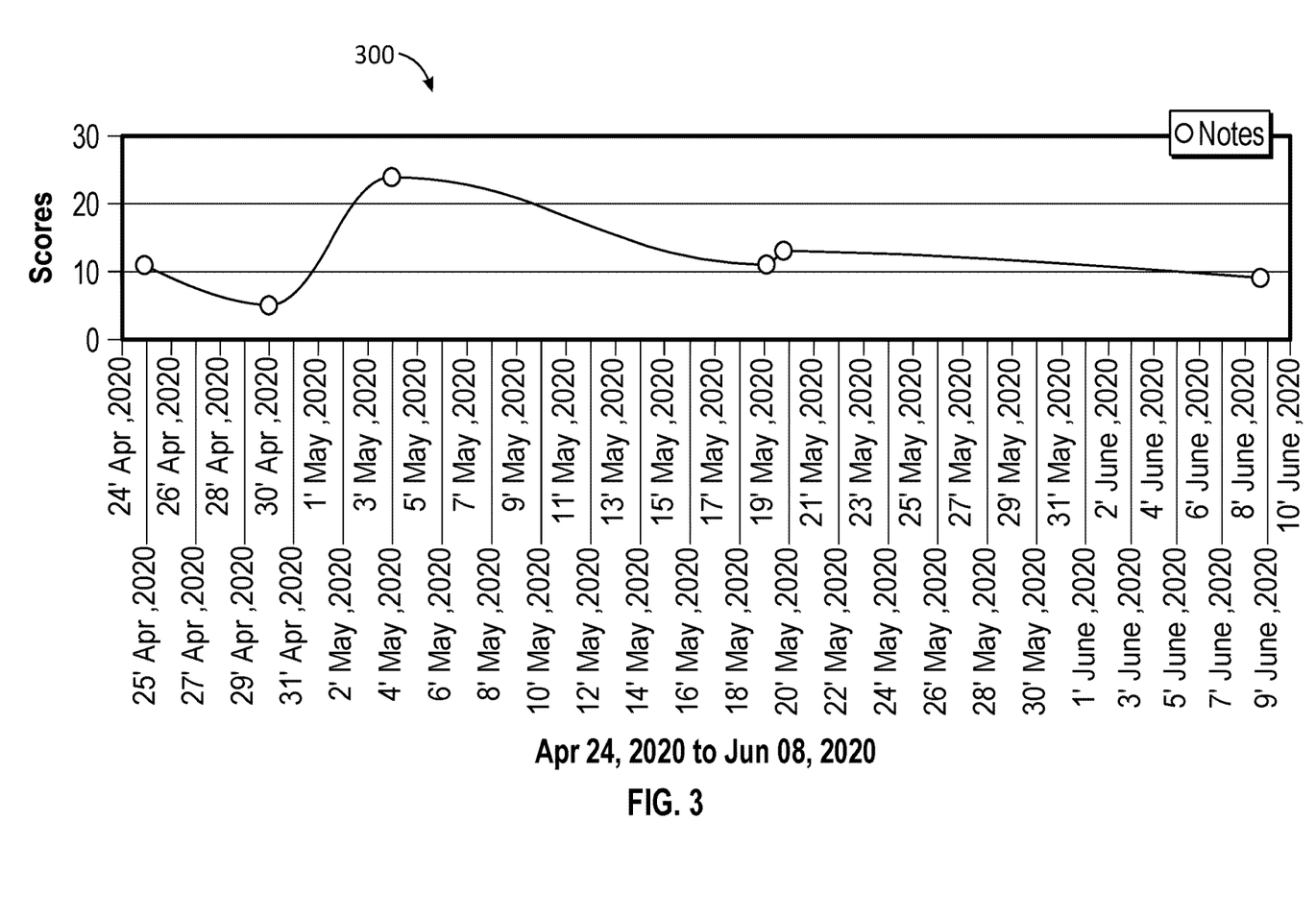
FIG. 3 depicts a computed wellness score and an overall treatment efficacy progress of the patient over a defined time duration.

FIG. 3 depicts a computed wellness score and an overall treatment efficacy progress of the patient over a defined time duration such as from Apr. 24, 2020 to Jun. 8, 2020, which may be represented in a patient history for each assessment type.

Figure 4:
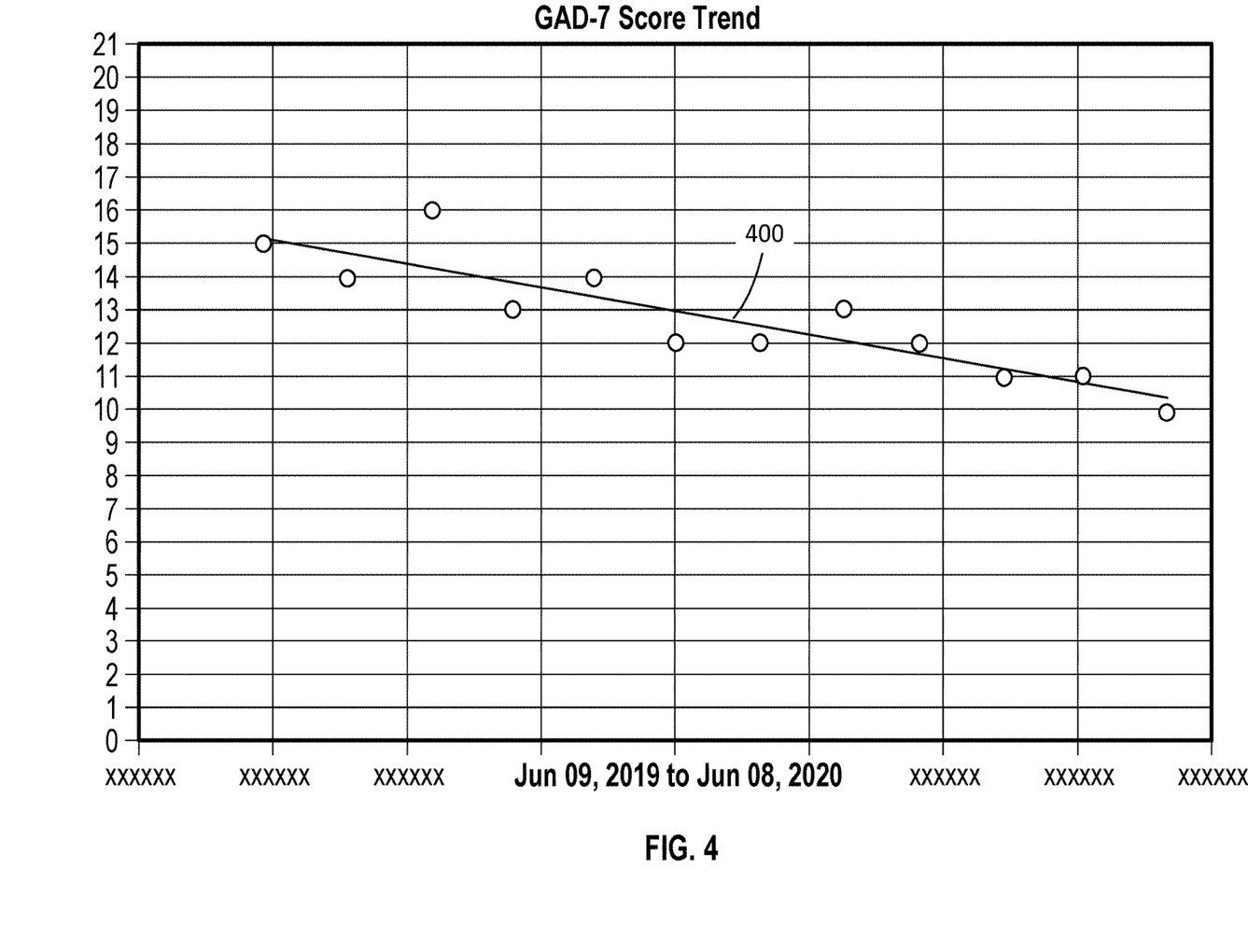
FIG. 4 depicts an example of a distribution of a gradient of the computed wellness scores of an overall treatment efficacy progress of the patient.

FIG. 4 depicts an example of a distribution of a gradient 400 of the computed wellness scores of an overall treatment efficacy progress of the patient over a defined period of time duration (e.g., Jun. 9, 2019 to Jun. 8, 2020). The gradient 400 may be indicate an improvement through a Per-Patient Rate of Change of Assessment Scores. The gradient may be calculated using a Least Squares approach linear regression, with removal of outliers for data points with a high Z-score, the system calculates and stores a rate of change for each patient's assessment score, for each applicable assessment type. This linear regression calculation may be done on a continuous basis (each time an assessment is taken by a patient), over a set of definable time period following the initiation of a treatment regimen for each patient.

The gradient of the computed wellness score for each individual patient may be calculated by a Least Squares fit on the wellness scores over the time duration of treatment. The formula for linear slope is as follows:

$$= \frac{\sum (x - \bar{x}) * (y - \bar{y})}{\sum (x - \bar{x})^2}.$$

wherein y is an instantaneous score, $\bar{y}$ is a mean score, x is an instantaneous time duration, $\bar{x}$ is a mean time duration. Outliers may be determined as any point whose distance from the linear fit is two standard deviations or greater. Since patient assessment score trends may be impacted greatly by a particularly "anomalous day" in the patient's history, this analysis assumes that a single (or small percentage, i.e., less than 10%) of scores that are outliers may be removed. Once these are excluded, the slope is recalculated based on remaining scores. If the total number of remaining scores is absolutely greater than four (4) across the designated time period, the gradient (i.e., slope) may be kept as valid for the overall sample; otherwise the patient assessment may be discarded for the particular assessment type. In an example, a linear regression best fit line 400 to GAD-7 patient score over time, showing a negative slope of approximately −0.4 points/month (improvement/lowering of anxiety) is shown in FIG. 4.

Figure 5:
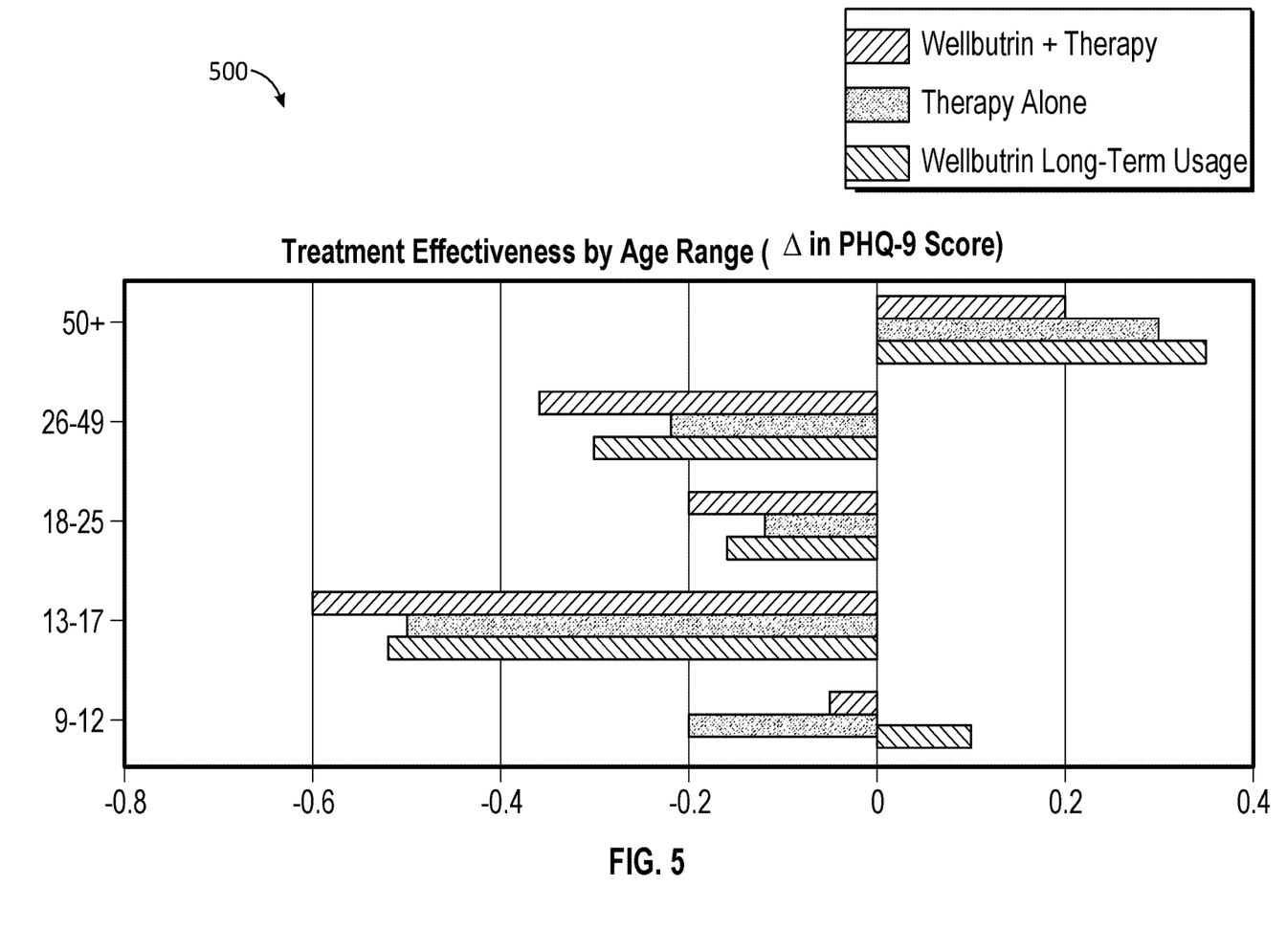
FIG. 5 depicts examples correlated coefficient of fixed factors and variable factors that affect the overall treatment efficacy progress within a pool of patients population.

FIG. 5 depicts examples of correlated coefficient of fixed factors and variable factors that affect the overall treatment efficacy progress for depression treatment within a pool of patients population, measured across different age ranges. In order to allow population factors to be specified and analyzed, with generation of correlations and reported views on relationships in the data: define Population Fixed and Variable Factors—The system 100 may enable a user to select from various stored population factors, in order to specify which are fixed and which individual factor is the independent variable to be analyzed for prevalence and correlation. For example, the user may select ethnicity as the independent variable, while other factors such as age range, gender and marital status as fixed. A fixed factor may be fixed at a specific value or at any fixed set of values. At this stage, cost factors for populations (e.g., cost per unit time) may also be provided as input, including average cost from lost productivity and average cost for treatment.

In an example, the fixed factors may be factors which are held constant for an analytic comparison across a population, which may include parameters such as: gender, occupation, ethnicity, religious belief, geographical location, and/or marital status, and the variable factors are factors to compare correlation which may change dynamically or change at a steady pace for statistical correlation analysis, may include parameters such as: age range vs. treatment efficacy across treatment types, or depression levels vs. prevalence of abrupt circumstantial events (e.g., job loss, divorce, relationship breakup, physical or emotional trauma, etc.)

Treatment effectiveness by age range may be determined by computing mean and median values for each population segment. Once a population segmentation is defined, the system 100 calculates the mean and median absolute assessment scores and rate of change of assessment scores for each segment stratified by its fixed factors and independent variable value. For prevalence calculations, the system may optionally allow either a first or a last value, within a date range, to be used for each patient. For a rate of change (e.g., mental health improvement) calculations, the computing layer 130 may enforce the exclusion of patients that do not satisfy assessment data collection within the minimum time period required post-initiation of the specified treatment regimen.

In order to ensure statistical validity, the computing layer 130 may calculate a P-value based on the number of data points in each segment of the population, as defined by the values of the independent variable and other set factors to validate a statistical significance of each dataset. An estimated total U.S. population size for demographic datasets with a specific mental illness may be obtained from the National Institute of Mental Health data, at https://www.nimh.nih.gov/health/statistics/mental-illness.shtml.

It should be noted that an acceptability of P-values may be configurable by the computing layer 130, with defaults set to less than or equal to 0.05. The validity of each segment may be reported on in the results. At this stage, costs for various treatment options in different segments may be determined and compared. To do this, a number of steps may be performed: (a) for each segment, determine a mean number of visits (outpatient and in-patient days) associated with each population segment; (b) for each segment, determine mean pharmaceutical dosage levels; (c) assign costs (input parameters) based on industry data for therapy, in-patient days, and prescription fees; (d) calculate mean cost per patient for each segment for specified time period (e.g. year) based on total visit, in-patient and prescription costs; (e) calculate the total demographic cost by segment by extrapolating the number of patients in the system's data to the total number of patients who fit each segment in a specified broader community, based on data gathered from the National Institute of Mental Health. As an example, various treatment options across a complete population may be compared with a costs for a total number of adults (1.3% of U.S. adult population) under a treatment for depression. Table 1 below may illustrate a compared cost for the treatment:

ficient may be calculated via Spearman's Correlation. For a rate of change analysis, mean and median may also be used, with Pearson's and Spearman's Correlation coefficients ρ calculated. All of these coefficients may be provided in the results, with higher coefficients (greater than 0.5) identified.

The linear correlation coefficient may include a Pearson's Correlation coefficient which is calculated as follows:

$$r = \frac{\sum(x-\bar{x})(y-\bar{y})}{\sqrt{\sum(x-\bar{x})^2}\sqrt{\sum(y-\bar{y})^2}}$$

wherein r is a treatment rank, wherein y is an instantaneous score, $\bar{y}$ is a mean score, $\bar{x}$ is an instantaneous time duration, x is a mean time duration.

The non-linear correlation coefficient may include a Spearman's Correlation coefficient ρ which may be calculated as follows:

$$\rho = 1 - \frac{6\sum d_i^2}{n(n^2-1)}$$

where $d_i = rq(x_i) - rg(y_i)$, which is a difference between the ranks (relative positions) of the two variables $rq(x_i)$ and $rg(y_i)$, and n=total number of observations.

In implementation, comparison tables and charts may be generated (such as FIG. 5), to output the above datasets in tables and graphs using a configured independent variable, with prevalence and rates of change plotted. This comparison may provide additional visual confirmation of any positive or negative correlation results. The output tables and charts may show, by population, prevalence and sociological cost of each condition, treatment correlation and effectiveness, and cost of treatment. The adjusting of the allocated mental health treatment resources may include increasing or reducing one or more of: estimated total benefits payable to medical treatment or therapy, estimated total prescription cost, estimated number of office visits or

| Treatment | Mean Outpatient Visits Per Patient | Mean In-Patient Days Per Patient | Mean Days of Pharma Usage | Total Cost Per Patient | % of Tracked Population | Total Treatment Cost for Larger Demographic ($B) |
|---|---|---|---|---|---|---|
| Outpatient Therapy | 14.7 | | | $1,617 | 27% | $1.46B |
| Therapy + Prescription (Wellbutrin) | 12.3 | | 142.6 | $1,441 | 52% | $2.50B |
| In-Patient + Follow-Up Therapy + Prescription | 11.5 | 16.1 | 195.2 | $6,538 | 21% | $4.59B |

Since the existence and type of correlation may be unknown, complete set of data points may be analyzed for both linear and non-linear correlation values. This analysis may be done via eight analyses for each included assessment type. For the prevalence dataset, the independent population variable may be mapped to the dependent variable, and calculated as the mean value of the sum of all assessment scores in each segment. The median value may also be done. Each of these has a linear correlation coefficient calculated via Pearson's Correlation, and a non-linear correlation coefconsultations, speech therapists visits, occupational therapists visits and new service requests.

The overall treatment efficacy progress may include providing comparative data regarding efficacy of treatment for non-mental health issues with the consideration of mental health comorbidity, wherein the comparative data of mental health comorbidity may include compared data of patient's rate of response to a treatment regimen including one or both of medication and counseling, wherein the patient is diagnosed with a spectrum of mental health condition.

As shown in FIG. 5, a dataset of results with statistically significant population sizes at each age range and treatment regimen for three treatment types-administration of long-term Wellbutrin usage (carryover from previous age range), Wellbutrin coupled with Regular Therapy, and Regular Therapy by itself-could are shown with the following results.:

In the examples shown, measurements would set to "Not Relevant" the variables of gender, ethnicity, geography, and all others, and would set age as the independent variable, and a rate of change of PHQ-9 score (over a designated timeframe of treatment) to be the dependent variable. An analysis may ignore patients who do not satisfy sufficient score quantity (on a relevant linear regression), and would ensure each patient age-range sample population is significant with a P-value less than or equal to 0.05.

The graph in FIG. 5 may indicate no linear or non-linear continuity with age, as the treatment regimens are more effective in teens and middle-ages than in pre-adolescent, young adult or older populations. In the event that it is desired for the analysis to determine whether there is a linear or non-linear relationship between the independent variable and dependent variable based on a logical ordering of the independent variable, the Pearson's and/or Spearman's correlation calculations may then be used. For example, treatment effectiveness may show a strong linear decline as proximity to a major geographic center increases with, for example, a Pearson's correlation coefficient of 0.8.

In another embodiment, the computing layer 130 may include utilizing an artificial neural network (ANN) $104n$ to train the algorithm to perform deep learning of the correlation of the coefficient of fixed factors and variable factors that affect the overall treatment efficacy progress within the pool of patients population in order to determine which factors are most strongly correlated with treatment success and which factors show little or no correlation. This determination may be used to advice on the next mental health treatment regimen for efficacy progress over the next time duration for the patient.

For example, the ANN $104n$ may be one of: a recursive neural network (RNN) model comprising layers of neurons having feedback loops for processing a one-time sequenced treatment regimen and a Graph Neural Network (GNN) model utilizing a message passing mechanism that fires neurons by processing a plurality of time sequenced treatment regimens over multiple time durations for evaluations. More specifically, the time sequenced treatment regimen may be the next mental health treatment regimen which is to be determined for the efficacy progress over an evaluation in the next time duration for the patient, by comparing each of the plurality of symptoms categories data of the patient with a peer group of a similar fixed factor or a variable factor to observe for a deviation of a particular symptom category that exceeds a specified normal distribution range in order to tabulate a list of anomaly for isolated symptoms for further study, wherein each isolated symptom is assigned with a statistical weight according to an extent of range deviation from the normal distribution.

In an example, the isolated symptoms in the list of anomaly for further study is targeted for adjustment of respective resources or assigning new resources for intervention in the next mental health treatment regimen in order to monitor for efficacy progress over the evaluation in the next time duration for the patient. In implementation, the deep learning of the correlation of the coefficient of fixed factors and variable factors that affect the overall treatment efficacy progress within the pool of patients population may include correlating for an efficacy progress in a next assessment of the patient within the peer group of a same coefficient of fixed factor or a same variable factor, and correlating an outcome of the isolated symptom category after a previous mental health treatment regimen; and updating the database layer for sharing of efficacy progress for public mental health improvement.

In another example, the results of the output $104r$ of the ANN $104n$ may be fed back to the computing layer 104 for a recursive training iteration for the same coefficient of fixed factor or the same variable factor to optimize treatment resource allocation for efficacy progress in a next treatment regimen.

While particular examples above have been illustrated and described herein, it should be understood that various other changes and modifications may be made without departing from the spirit and scope of the claimed subject matter. Moreover, although various aspects of the claimed subject matter have been described herein, such aspects need not be utilized in combination. Accordingly, it will be appreciated that the above described examples should not be construed to narrow the scope or spirit of the disclosure in any way. Other examples, embodiments, aspects, and advantages will become apparent from the following detailed description taken in conjunction with the accompanying drawings. It is therefore intended that the appended claims cover all such changes and modifications that are within the scope of the claimed subject matter.

What is claimed is:

1. A computer implemented method for allocating resources in mental health treatment, comprising:
   executing, by at least one processor on a computing layer, an algorithm stored on a non-transitory computer-readable memory medium comprising:
   retrieving, from a database layer that stores individual patients' profiles and corresponding electronic medical records, a patient's mental health assessment data comprising one or more symptoms categories data that have been mapped to one or more assessed mental conditions;
   computing, a wellness score for the patient, by aggregating a plurality of individual weighted scores of the mapped assessed mental condition of the patient;
   determining, an overall treatment efficacy progress for the patient, by statistically analyzing a gradient of the computed wellness scores of the patient over a time duration;
   aggregating, over a pool of a patient population with similarly mapped assessed mental conditions, a distribution of the gradient of the computed wellness scores of an overall treatment efficacy progress;
   sampling over a defined range of the distribution of the gradient of the computed wellness scores of the overall treatment efficacy progress to determine a correlation coefficient of fixed factors and variable factors that affect the overall treatment efficacy progress within the pool of the patient population, wherein the fixed factors that do not change from assessment to assessment while variable factors are factors that can change from assessment to assessment;
   using both the correlated coefficient of fixed factors and variable factors to compare or adjust treatment efficacy results over a range of available mental health treatment resources to determine a mental health treatment regimen with an optimal overall efficacy progress over a next time duration for the patient;

communicating the next mental health treatment regimen, along with a level of confidence factor, to a healthcare provider for requesting the resources for the patient; and distributing assessments to patients or designated intermediaries.

2. The method according to claim 1, wherein the retrieved patient mental health assessment data are collected from devices from one or a combination of: the patient, the health care provider and an authorized responder intermediary, and wherein the patient's mental health assessment data comprising one or more of following information:
- standardized questionnaire responses;
- physiological vital signs-measurements;
- drug treatment clinical data;
- behavioral or mood observation data;
- learning disabilities or speech delays in childhood or adolescence;
- substance abuse or chemical dependence;
- observed physical gestures;
- observed physical abuse or self-inflicted wounds; and
- social media blogs, posts, or messages containing contextual content manifesting symptoms of mental distress, aggressiveness, depression, or suicidal thoughts.

3. The method according to claim 1, wherein:
the profile of the patient comprising one or more of: name, age, gender, residence geographic location, ethnicity, marital status, education level, employment status, and income level; and
the patient mental health assessment data comprising one or more of:
- medication information;
- physical health data;
- obesity data;
- mental health history;
- physiological data;
- history of substance abuse;
- family healthy history;
- history of anxiety, depression, attention-deficit/hyperactivity disorder (ADHD), obsessive compulsive disorder (OCD), substance addiction, bipolar disorder, suicidal thoughts, or trauma; and
- significant life events.

4. The method according to claim 3, wherein an identity of the patient is replaced with a unique but anonymous personal identification for privacy protection.

5. The method according to claim 1, comprising one or more of the following:
- enabling clinics to run assessments on demand or on a scheduled basis, with timing or frequency recommended or calculated based on past history and weighted specific conditions;
- distributing assessments to patients or designated intermediaries on the communication device, for completion in office, at home or in any Internet-available location;
- gathering assessment data in a structured, relational database, including calculated levels of mental health disorder; and
- viewing of results by mental health professionals.

6. The method according to claim 1, wherein the collecting of the patient mental health assessment data comprising collecting through an Electronic Medical Record (EMR) or Electronic Health Record (EHR) systems.

7. The method according to claim 2, wherein the physiological vital signs measurements are measured by clinical devices or instruments, where such vital signs measurements comprising one or more of: blood pressure, heart rate, heart rate variability (HRV), and breathing rate variability.

8. The method according to claim 2, wherein the observed physical gestures comprising one or more of: voice analysis, eye blink rates and jaw clenching.

9. The method according to claim 1, wherein the computing of the wellness score for the patient comprising assigning a weight to each category of information in the patient mental health assessment data and computing a weighted sum.

10. The method according to claim 9, wherein the gradient of the computed wellness score for each individual patient comprising calculating a least squares fit of a linear regression on the wellness scores over the time duration of treatment, wherein the Least Squares fit is as follows:

$$= \frac{\sum (x - \bar{x}) * (y - \bar{y})}{\sum (x - \bar{x})^2}$$

wherein y is an instantaneous score, $\bar{y}$ is a mean score, x is an instantaneous time duration, and $\bar{x}$ is a mean time duration.

11. The method according to claim 2, wherein the fixed factors are factors which are held relatively constant for an analytic comparison across a population, comprising: gender, occupation, ethnicity, religious belief, geographical information, and/or marital status, and wherein the variable factors are factors to compare for statistical correlation, comprising age range, data from the allocated mental health treatment resources, and abrupt circumstantial events.

12. The method according to claim 1, wherein the correlation coefficient is one of a linear correlation coefficient or a non-linear correlation coefficient, wherein the linear correlation coefficient comprising a Pearson's Correlation coefficient calculated as follows:

$$r = \frac{\sum (x - \bar{x})(y - \bar{y})}{\sqrt{\sum (x - \bar{x})^2} \sqrt{\sum (y - \bar{y})^2}}$$

wherein r is a treatment rank, y is an instantaneous score, $\bar{y}$ is a mean score, x is an instantaneous time duration, and $\bar{x}$ is a mean time duration,
the non-linear correlation coefficient comprising Spearman's Correlation coefficient ρ, calculated as follows:

$$\rho = \frac{6 \sum d_i^2}{n(n^2 - 1)}$$

where $d_i = rq(x_i) - rg(y_i)$, which is a difference between ranks or relative positions of two variables $rq(x_i)$ and $rg(y_i)$, and n=total number of observations.

13. The method according to claim 1, wherein the adjusting of the allocated mental health treatment resources comprising increasing or reducing one or more of: estimated total benefits payable to medical treatment or therapy, estimated total prescription cost, estimated number of office visits or consultations, speech therapist visits, occupational therapist visits, and new service requests.

14. The method according to claim 1, wherein the overall treatment efficacy progress comprising providing comparative data regarding efficacy of treatment for non-mental health issues with the consideration of mental health comorbidity.

15. The method according to claim 14, wherein the comparative data of mental health comorbidity comprising compared data of patient's rate of response to a treatment regimen comprising one or both of medication and counseling, wherein the patient is diagnosed with a spectrum of mental health conditions.

16. The method according to claim 11, comprising utilizing an artificial neural network (ANN) to train the algorithm to perform deep learning of the correlation of the coefficient of fixed factors and variable factors that affect the overall treatment efficacy progress within the pool of patients population in order to determine which factors are most strongly correlated with treatment success or factors that show little or no correlation in order to advise the next mental health treatment regimen for efficacy progress over the next time duration for the patient.

17. The method according to claim 16, wherein the ANN comprises one of:
 a recursive neural network (RNN) model comprising layers of neurons having feedback loops for processing a one-time sequenced treatment regimen; and
 a Graph Neural Network (GNN) model utilizing a message passing mechanism that fires neurons by processing a plurality of time sequenced treatment regimens over multiple time durations for evaluations.

18. The method according to claim 17, wherein the timed sequenced treatment regimen being the next mental health treatment regimen which is to be determined for the efficacy progress over an evaluation in the next time duration for the patient, by comparing each of the one or more symptoms categories data of the patient with a peer group of a similar fixed factor or a variable factor to observe for a deviation of a particular symptom category that exceeds a specified normal distribution range in order to tabulate a list of anomaly for isolated symptoms for further study, wherein each isolated symptoms is assigned with a statistical weight according to an extent of range deviation from the normal distribution.

19. The method according to claim 18, wherein the isolated symptoms in the list of anomaly for further study is targeted for adjustment of respective resources or assigning new resources for intervention in the next mental health treatment regimen in order to monitor for efficacy progress over the evaluation in the next time duration for the patient.

20. The method according to claim 16, wherein the deep learning of the correlation of the coefficient of fixed factors and variable factors that affect the overall treatment efficacy progress within the pool of patients population comprising correlating for an efficacy progress in a next assessment of the patient within the peer group of a same coefficient of fixed factor or a same variable factor, and correlating an outcome of the isolated symptom category after a previous mental health treatment regimen; and updating the database later for sharing of efficacy progress for public mental health improvement.

\* \* \* \* \*